(12) United States Patent
Simms et al.

(10) Patent No.: US 9,579,090 B1
(45) Date of Patent: Feb. 28, 2017

(54) SURGICAL INSTRUMENT WITH MULTIPLE INSTRUMENT INTERCHANGEABILITY

(71) Applicants: Eric Simms, New Orleans, LA (US); Joseph Young, Redlands, CA (US); Jordan Vance, Mt. Vernon, OH (US)

(72) Inventors: Eric Simms, New Orleans, LA (US); Joseph Young, Redlands, CA (US); Jordan Vance, Mt. Vernon, OH (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 433 days.

(21) Appl. No.: 14/189,221

(22) Filed: Feb. 25, 2014

Related U.S. Application Data

(60) Provisional application No. 61/769,957, filed on Feb. 27, 2013.

(51) Int. Cl.
*A61B 18/00* (2006.01)
*A61B 17/00* (2006.01)
(Continued)

(52) U.S. Cl.
CPC ......... *A61B 17/00234* (2013.01); *A61B 18/08* (2013.01); *A61B 2017/00464* (2013.01); *A61B 2017/3445* (2013.01)

(58) Field of Classification Search
CPC ................... A61B 5/0422; A61B 2017/00464; A61B 2017/22075; A61B 2018/00166; A61B 2017/00225; A61B 2017/3447; A61B 2017/22072; A61B 2017/3445; A61B 2017/3449
See application file for complete search history.

(56) References Cited

U.S. PATENT DOCUMENTS

| 5,312,391 A | 5/1994 | Wilk |
|---|---|---|
| 5,456,695 A | 10/1995 | Herve Dallemagne |

(Continued)

FOREIGN PATENT DOCUMENTS

| EP | PCT/IB2011/052058 | 3/2012 |
|---|---|---|
| NZ | PCT/NZ2005/000263 | 4/2006 |

OTHER PUBLICATIONS

Bergamaschi R, Arnaud JP. Immediately recognizable benefits and drawbacks after laparoscopic colon resection for benign disease. Surg Endosc 1997; 11: 802-804.
(Continued)

*Primary Examiner* — Jocelyn D Ram
(74) *Attorney, Agent, or Firm* — Emily L. Gordy; Ian C. Barras; Carver, Darden, Koretzky, Tessier, Finn, Blossman & Areaux, LLC

(57) ABSTRACT

The present invention provides a multi-function laparoscopic surgical instrument that meets niche needs in the expanding field of Minimally Invasive Surgery (MIS). A preferred embodiment of the present invention comprises a sheath that may be inserted into a patient, wherein the sheath contains at least two interchangeable surgical instruments that may be advanced into or retracted from the patient through a single outlet in the sheath. It is intended for use in laparoscopic and thoracoscopic surgical procedures, including intra-abdominal, intra-thoracic, intra-pelvic and arthroscopic MIS procedures, and is particularly well suited to single incision laparoscopic surgery and Natural Orifice Translumenal Endoscopic Surgery (NOTES).

19 Claims, 12 Drawing Sheets

(51) Int. Cl.
*A61B 18/08* (2006.01)
*A61B 17/34* (2006.01)

(56) References Cited

U.S. PATENT DOCUMENTS

| | | | | |
|---|---|---|---|---|
| 5,685,877 | A | * | 11/1997 | Pagedas ............. A61B 18/1482 600/106 |
| 5,755,713 | A | * | 5/1998 | Bilof ................ A61B 17/00234 600/104 |
| 5,766,169 | A | * | 6/1998 | Fritzsch ............. A61B 17/2909 606/46 |
| 5,776,092 | A | * | 7/1998 | Farin ................ A61B 17/22012 604/22 |
| 5,954,731 | A | * | 9/1999 | Yoon .................... A61B 17/062 606/139 |
| 6,506,208 | B2 | | 1/2003 | Hunt et al. |
| 6,706,050 | B1 | | 3/2004 | Giannadakis |
| 7,156,839 | B2 | | 1/2007 | Bayer et al. |
| 2005/0096502 | A1 | | 5/2005 | Khalili |
| 2006/0122629 | A1 | * | 6/2006 | Skakoon ................ A61B 90/11 606/130 |
| 2007/0049908 | A1 | * | 3/2007 | Boese .................... A61B 90/00 606/1 |
| 2008/0221602 | A1 | * | 9/2008 | Kuehner ............ A61B 17/3203 606/167 |
| 2010/0057078 | A1 | * | 3/2010 | Arts ....................... A61B 10/06 606/41 |

OTHER PUBLICATIONS

Ortega AE, Hunter JG, Peters JH, Swanstrom L, and Schirmer B. A prospective, randomized comparison of laparoscopic appendectomy with open appendectomy. Am J Surg 1995; 169: 208-212.

Fletcher DR, Hobbs MS, Tan P, Valinsky LJ, Hockey RL, Pikora TJ, Knuiman MW, Sheiner HJ, and Edis A. Complications of cholecystectomy: risks of the laparoscopic approach and protective effects of operative cholangiography: a population-based study. Ann Surg 1999; 229(4): 449-457.

Joice P, Hanna GB, and Cuschieri A. Errors enacted during endoscopic surgery—a human reliability analysis. Appl Ergon 1998; 29: 409-414.

Lam A, Kaufman Y, Khong SY, Liew A, Ford S, Condous G. Dealing with complications in laparoscopy. Best Practice & Research Clinical Obstetrics and Gynaecology 2009; 23: 631-646.

Savader SJ, Lillemoe K, Prescott CA, et. al. Laparoscopic cholecystectomy-related bile duct injuries: a health and financial disaster. Ann Surg 1997; 225(3): 268-73.

Kapoor VK, Pottakkat B, Jhawar S, Sharma S, Mishra K, Singh N, Vijayahari R. Costs of management of bile duct injuries. Trop Gastroenterol 2011; 32(2): 117-21.

Preston JM. Iatrogenic ureteric injury: common medicolegal pitfalls. BJU Int 2000; 86(3): 313-7.

Lau Wy, Lai EC, Lau SH. Management of bile duct injury after laparoscopic cholecystectomy: a review. ANZ J Surg 2010; 80: 75-81.

* cited by examiner

SURGICAL INSTRUMENT WITH MULTIPLE INSTRUMENT INTERCHANGEABILITY

CROSS REFERENCE TO RELATED APPLICATIONS

The application claims the benefit of priority of U.S. provisional patent application 61/769,957, filed Feb. 27, 2013, said application being incorporated herein by reference.

BACKGROUND

During a simple laparoscopic cholecystectomy performed by an experienced surgeon, instruments are switched through the trocars (body cavity surgical access ports) approximately ten to fifteen times. For more complex laparoscopic cholecystectomies, instruments may need to be switched greater than 50 times. More complex minimally invasive surgeries (e.g. laparoscopic hemicolectomies, laparoscopic adrenalectomies, etc.), or more challenging patient characteristics can necessitate even more instrument switching, sometimes hundreds of times per case.

Examples of patient characteristics that may necessitate increased instrument switching include, but are not limited to: presence of "adhesions" (internal scar tissue) from inflammatory processes or previous operations, aberrant anatomy or variations in normal anatomy, weight/patient body habitus (large Body Mass Index (BMI)), and/or complicating disease masses/structures. Given an accurate estimation of 3 to 30 seconds of time per instrument switch, instrument switching therefore accounts for unnecessarily increased operative times. After multiple instrument switches, instrument switching accounts for excess minutes to hours of operative time, depending on case complexity or overall operative time.

Currently, during Minimally Invasive Surgery (MIS), multiple incisions are made in the abdomen, pelvis, thorax or extremity joint spaces, with a "trocar" placed in each incision to serve as a portal for instrument entry into the body cavity. The trocars also serve as one-way valves, allowing instruments to be placed into and removed from body cavities, while not allowing $CO_2$ (used to insufflate the body cavity) to escape during instrument switching or removal. Typically multiple MIS instruments and a laparoscopic camera are required. Frequent instrument switching is almost universally required during MIS, and comprises a significant proportion of MIS case time. Every time an instrument is switched for another, the currently used instrument is removed from the body cavity (usually under direct visualization of the camera) and set down. The electrocautery cable is disconnected from the instrument and reconnected to the next desired instrument. This step requires two hands, either requiring an assistant, or requiring the surgeon to let go of other instruments in order to change the electrocautery cable.

Once the new desired instrument is connected to the electrocautery cable, said instrument is replaced through the trocar into the body cavity to be used. Although this series of actions only takes several seconds to accomplish, the action is required tens to hundreds of times per laparoscopic surgery. The redundancy of motion contributes significantly to increased surgical time and loss of economy of motion, and often requires the surgeon to change visual focus, also increasing surgical time, and compromising safety. Increased surgical time translates directly into increased healthcare costs for surgery centers and hospitals. It also increases patient exposure to: volatile anesthetic agents, non-ergonomic surgical body positioning (with concomitant neurologic risk), hypothermia, excess tissue stress from insufflation and instrument manipulation, and surgical team fatigue during long cases. The excess movement of instruments into and out of body cavities not only increases time, but also the risk of iatrogenic injury (accidental, surgeon-caused injury, e.g. perforation or electrocautery burn) to internal organs and structures. Iatrogenic injury during surgery is another source of excess healthcare costs, both for costly surgical repairs of damaged structures, and for lawsuits associated with such injuries.

Excess time is wasted on instrument switching, resulting in longer operative times, and unnecessary patient safety risks. Examples of wasted time include when: the operation requires a multitude of instrument switches; the electrocautery cord needs to be switched between instruments; the physician needs to adjust grip on other instruments, or switch hands, during switching maneuvers; the physician must take focus away from internal structures, so they need to change the focus of their eyes to perform instrument switches (and re-focusing takes time); the physician needs to "follow" the previous instrument out with the laparoscopic camera, and "follow" the new instrument back in with the camera to perform the switch safely, therefore the physician must reorient themselves with respect to the structures/organs being manipulated when the camera returns its focus to the surgical site (sometimes taking minutes, especially if other tissues or structures fall into the view of the camera and need to be held out of the way repetitively); getting blood/fluid on the camera while moving it around to "follow" instruments, necessitating more time spent cleaning the camera (which often needs to be removed to be cleaned); and, instruments accidentally drop off the sterile field, so time/efficiency/money is wasted on getting new instruments, or sterilizing the previous one. Increased operative time results in decreased efficiency for hospitals and Operating Rooms (ORs).

Further examples of safety being sacrificed as a result of instrument change-out include when: the surgeon does not "follow" instruments in/out of body cavities with the camera, increasing risk of iatrogenic injury to internal structures, such as bowel/other organ perforation; the surgeon has to change visual focus, or shift attention rapidly (again risk of perforation, sheering injury, traction injury, etc.); the surgeon becomes fatigued from increased operative times; extraneous movement inside body cavities increases the likelihood of accidental injury/perforation/thermal injury; extraneous movement inside body cavities causes excess tissue trauma, especially at the trocar sites which are often re-angled multiple times during instrument switching; thermal injury to skin occurs from removing previously used electrocautery instruments out of body and setting somewhere else on the patient; increased operative times results in increased exposure to potentially hazardous surgical environmental conditions (e.g. volatile anesthetics; non-ergonomic body positioning, with increased risks of ischemia (especially to extremities), nerve compression, and muscle necrosis with increased time; operating room conditions, especially hypothermia; and insufflation of body cavities with $CO_2$: excess/prolonged exposure increases the risk of tissue ischemia from increased pressure in abdomen—vasculopaths and pregnant women (gravid uterus) are particularly at risk).

All factors that increase the risk of iatrogenic/accidental injury to the patient place hospitals, hospital systems, surgery centers, and physicians at increased risk of litigation, and are socially, economically, and legally hazardous. Unnecessary injuries to patients are associated with multiple problems for patients and patient families, including loss of life or function, excess pain and suffering, and economic and psychosocial distress if family members die or are unable to work. It is also associated with multiple problems for hospitals and physicians, such as lawsuits, increased malpractice rates, and the economic and resources-based burdens of further procedures to repair iatrogenic injuries, longer hospital stays, and more clinic (follow-up) visits to address the injuries.

Several multi-function laparoscopic devices have been disclosed. However, these instruments are either crude, overly complicated for the surgeon to use, or do not allow for flexibility as to which instruments are used. There are a few points in particular that illustrate problems with prior disclosures. First, many are designed specifically for robots as opposed to surgical hands. Second, many have multiple exit points for the instruments which make it difficult for the surgeon to manage as well as fit in tight spaces within the body. Third, many limit the device to set instruments as opposed to providing the surgeon flexibility on which instruments to use. Fourth, they do not allow advancement or retraction of these instruments into and out of the body with selection of each instrument. Fifth, they do not allow automated changing of instruments mid-procedure, without removing the instruments from the body.

A device is needed that provides surgeons comfort and flexibility to use any laparoscopic instrument she or he desires while not compromising safety for the patient.

While certain novel features of this invention shown and described below are pointed out in the claims, the invention is not intended to be limited to the details specified herein, since a person of ordinary skill in the relevant art will understand that various omissions, modifications, substitutions and changes in the forms and details of the invention illustrated, and in its operation, may be made without departing in any way from the spirit of the present invention. No feature of the invention is critical or essential unless it is expressly stated as being "critical" or "essential."

SUMMARY OF THE INVENTION

The present invention provides multiple advanceable and retractable instruments in a single sheath, with automated advancing and retracting. Instruments which are in the advanced ("engaged") position may retract automatically when the next instrument is selected (advanced to the engaged position). Instruments may be exchangeable/interchangeable within the main sheath, allowing a surgeon to select a specific array of instruments ("instrument profile") to suit their preferences or to suit the specific surgery to be performed. All of the individual instruments may have electrocautery capability through a single connection port on the main housing sheath.

In accordance with this discovery, it is an object of the invention to provide a surgical device with rapid advancement/retraction of laparoscopic/thoracoscopic/minimally invasive surgical instruments via a single sheath, without the need to remove the main instrument (sheath) in order to switch instruments.

It is another object of the invention to reduce the time required to perform safe minimally invasive (or laparoscopic, thoracoscopic, arthroscopic, pelvic, single incision laparoscopic surgery, and/or Natural Orifice Translumenal Endoscopic Surgery—"NOTES") surgical procedures by decreasing the time currently used for instrument switching.

An object of the invention is to decrease instrument switching time and decrease extraneous movement inside body cavities, based on instrument switching.

It is another object of the invention to increase the economy of motion thereby decreasing the amount of instrument movement inside body cavities and decreasing the chance of iatrogenic injury.

It is another object of the present invention to provide a surgical instrument particularly suited for MIS, including NOTES and Single-Incision Laparoscopic Surgery (SILS). By decreasing the length of MIS, it is another object of the invention to decrease surgical costs, as well as exposure of the patient to anesthetics, non-ergonomic positioning, tissue stress, hypothermia, and surgical team fatigue. The decreased motion of surgical instruments inside body cavities also decreases the risk of iatrogenic surgical injury, and the costs associated with such injury.

While the disclosure provides certain specific embodiments, the invention is not limited to those embodiments. A person of ordinary skill will appreciate from the description herein that modifications can be made to the described embodiments and therefore that specification is broader in scope than the described embodiments. All examples are therefore non-limiting.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
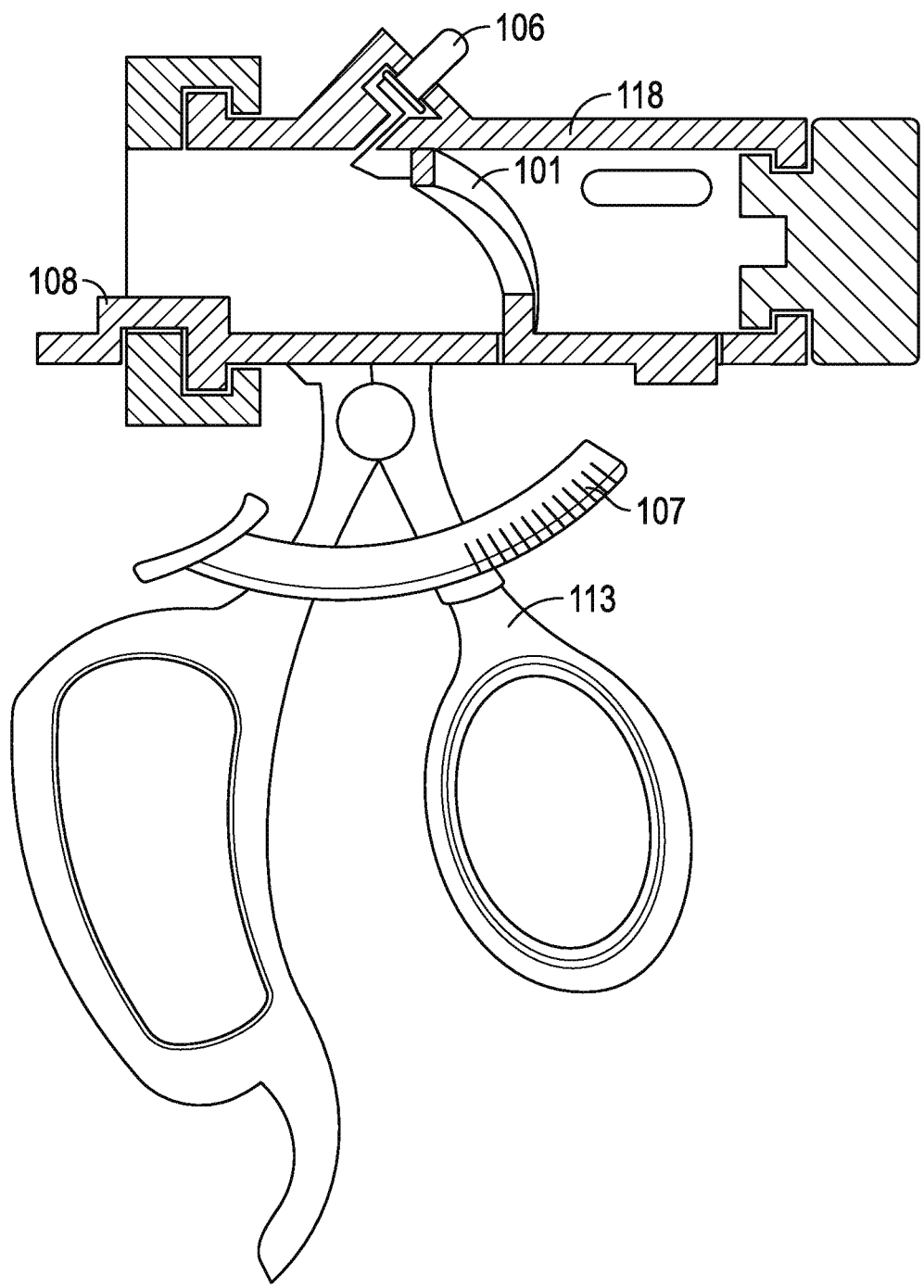
FIG. 1: An exemplary design of the proximal portion of the device.

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Wherever the phrase "for example," "such as," "including" and the like are used herein, the phrase "and without limitation" is understood to follow unless explicitly stated otherwise. Similarly "an example," "exemplary" and the like are understood to be non-limiting.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c.

Wherever the terms "a" or "an" are used, "one or more" is understood, unless such interpretation is nonsensical in context.

The "proximal" end of the device is the portion nearest where the surgeon holds the device. The "distal" end of the device is the portion that enters the patient.

One embodiment comprises a laparoscopic device, with multiple instrument interchangeability, each having electrocautery capability. The instrument houses multiple instruments within a single housing sheath. The instruments within the housing sheath are then interchangeable with different laparoscopic instruments (grasper, scissors, hook, etc. . . . ) in order to cater towards a specific surgical operation, or the personal preference of the surgeon.

In one embodiment, instruments remain housed within a housing sheath until rotated, and thus advanced forward. In one embodiment, only one instrument may advance forward at any given time. In one embodiment, the instrument being used must be at the top of the inside of the housing sheath at position (N) before it can advance. In order to change an instrument, a knob must be turned. The turning of the knob moves all of the instruments in a cyclic motion much like that of revolver (i.e., when bullet x is fired through barrel N, bullet x+1 revolves clockwise replacing bullet x at the same barrel N). During the turning of the knob, instrument x is retracted. As x retracts, instrument x+1 replaces it at position N, and then advances forward taking its place. A safety mechanism is put in place that prevents instrument x from retracting while the instrument is holding on, or clasping down, on any object. This ensures that no tissue will be unintentionally torn out of the patient when the knob is turned to change the instruments.

Within the housing sheath, the instrument being used is capable of individual rotation, allowing increased dexterity during operation. A gear is attached to the outside of each individual instrument, and an inner gear is attached to the barrel of the laparoscopic tool, which surrounds the housing sheath. When an individual instrument is rotated and moved into position N by the knob, the gear teeth on the outside of the individual instrument slides into position with the parent gear attached to the barrel.

Instruments that may be used with this device include: cameras/camera scopes, and other telescopes/telescopic instruments, including angled scopes; non-camera visualization sheaths (fiber-optics, etc.); light sources; insufflators/body cavity inflators; suction apparatus; irrigation/flushing apparatus (for fluids/liquids, including medications and powders such as chemotherapy agents, talcum powder, and aerosolized chemical/biological substances); cautery instruments, including "Bovie" electrocautery, electrocautery capable instruments, argon cautery, gas-based cautery instruments, laser attachments, and other heated probes; radiographic and ultrasonographic instruments; radiofrequency ablative instruments and probes; atraumatic graspers (including all other names for such graspers, such as "bowel graspers", "anti-traumatic graspers", "alligator graspers", etc.); toothed graspers; curved dissectors, straight dissectors; clip applicators/clip appliers, including loaded/loadable/loadable clips; dissection hooks/"L-tipped" instruments; scissors/curved scissors/hook scissors/micro scissors; surgical spatula/cautery spatula; forceps/retrieving forceps; needle holders; electrosurgical generators/monitors; biopsy needles/tissues samplers, including punch/needle/spoon biopsy instruments; "maryland" dissectors, including straight/curved/tapered/toothed/blunt; staplers, including gastrointestinal anastomotic staplers, thoracic staplers, end-to-end staplers, and other proprietary staplers; right-angled forceps/dissectors; specialty dissectors and graspers, including 90-degree angle graspers/dissectors, pointed/bullet/bottle/dolphin-nosed dissectors/graspers; all other dissectors/graspers (including, without limitation, micro, duck, duck-nosed, duck-billed, curved, blunt, round, fenestrated, standard, fine-toothed, tapered, strong arched, atraumatic, short, wave, serrated, clawed, bowel, DeBakey, Allis, Babcock, Ponce, Rodriguez, Uddo, Kocher, double-action, single-action, Oviduct, MoKernan, tri-grasping, Murray, Glassman, Pennington, extracting, angled, right-angled, Mixter, heavy, paddled, tenaculum, etc.); suturing materials, including all needle and suture types, and proprietary suturing instruments and needle passers and pushers; specialty/proprietary tipped instruments, including but not limited to: spatula, spoon, ball-tipped, J-hook, L-hooked, L-tipped, wedge, square, needle-tipped, button-tipped, flat, Corson, hooked, and spatulated; stopcocks, valves, and fluid tubing; and all bipolar instruments, forceps, and graspers; all proprietary instruments, including bags/"Endocatch" bags, retrieval bags, harmonic scalpels, electric scalpels, LigaSure devices, etc.

Figure 11A:
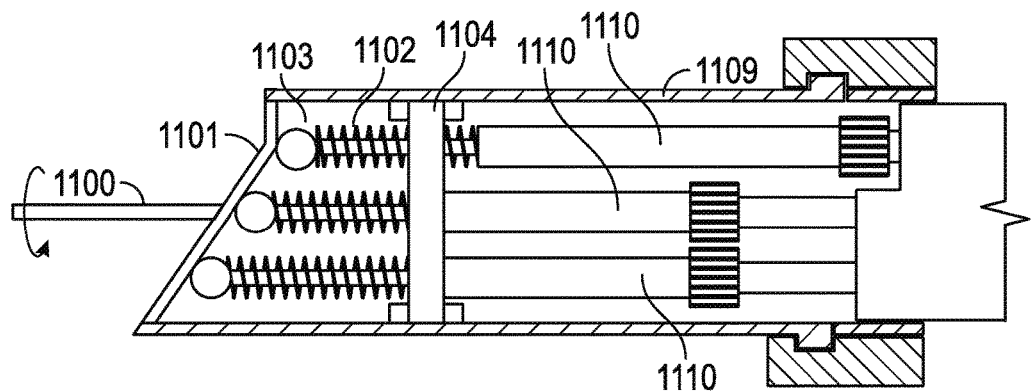
FIG. 11(A): An exemplary design where the instruments are spring loaded.

In a preferred embodiment, as shown in FIG. 11A, the present invention comprises a sheath 1109 in which a turning rod 1100 passes through the sheath 1109 and is attached to a turning disk 1104 within the sheath 1109. The turning disk 1104 may have three laparoscopic instruments 1110 passing through and locked to the disk 1104, such that when the turning rod 1100 is rotated, so is the turning disk 1104, thereby rotating the instruments 1110 within the sheath 1109. The instruments 1110 may be spring loaded 1102 in the sheath and/or the proximal end of the device may have an advancing ridge 1101. As the instruments are rotated within the sheath 1109, the proximal portions of the instruments move along the advancing ridge 1101 pushing them through the sheath 1109 or retracting them into the sheath 1109. This mechanism allows only a single instrument to be outside the distal end of the device, while the rest are securely housed within the sheath.

Figure 11B:
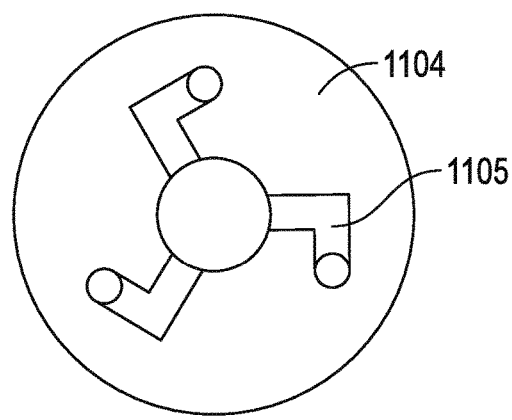
FIG. 11(B): An exemplary turning disk with locks for the instruments, highlighting instrument swap without use of a button.

FIG. 11A depicts an embodiment with a turning rod 1100 at the proximal end of the device, which passes through a sheath 1109. An advancing ridge 1101 allows each pushing rod spring assembly 1102 to advance or retract by pushing up against a sphere 1103 at the proximal end of the device. A turning disk 1104 maintains distance between the instruments 1110 as the turning rod is rotated. As shown in FIG. 11B, the turning disk 1104 may include a locking design 1105 for individual instrument interchangeability.

Figure 4:
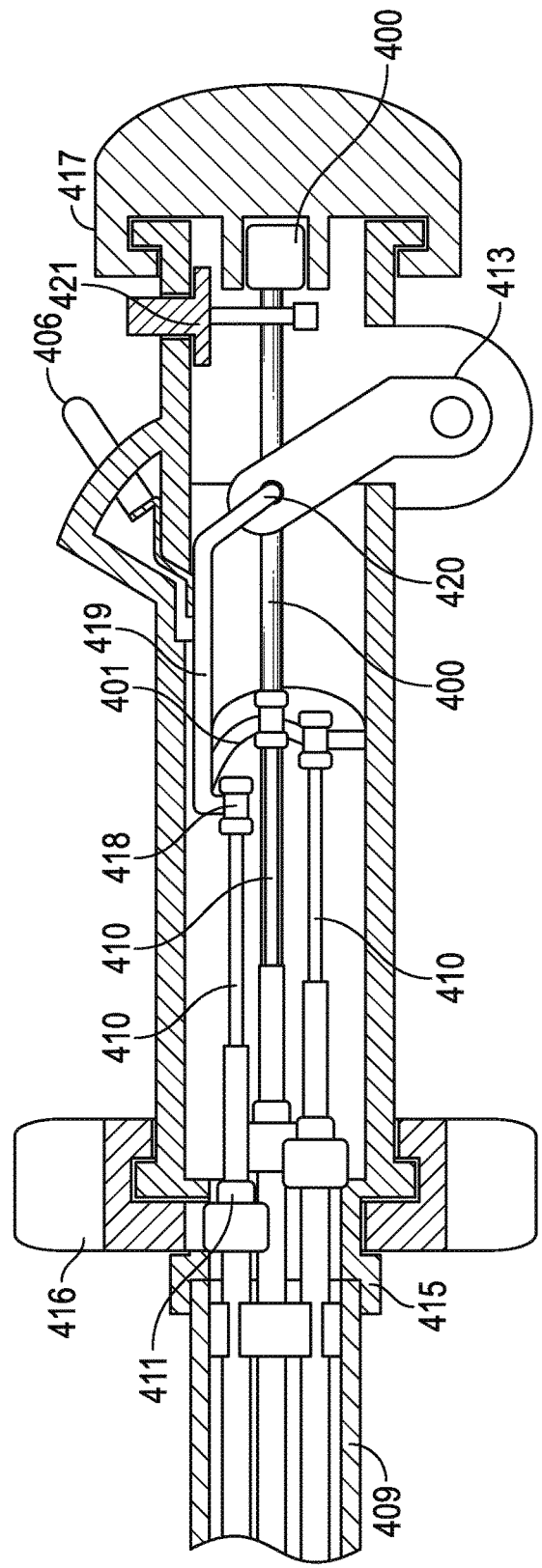
FIG. 4: An exemplary design of a sheath including different instruments, a gear system for individual instrument rotation, an electrocautery connection port on advanced instrument, a knob for switching instruments, a spool and ridge for advancing, retracting and guiding rotation of instruments, a rod for opening and closing instruments, an instrument release button.
Figure 7A:
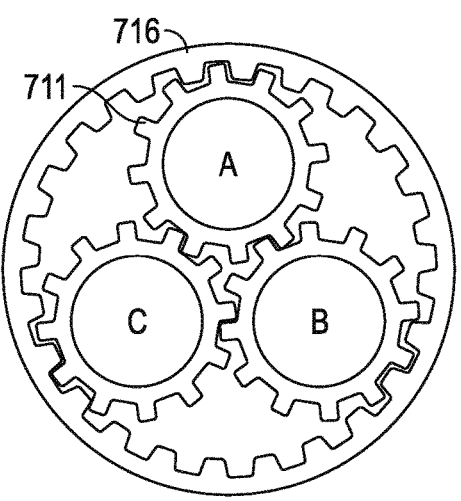
FIG. 7(A): An exemplary design for a gear system located in the barrel that allows only one instrument to be rotated at a time.

In one embodiment, as shown, for example, in FIG. 4, as a turning rod 400 or knob 417 rotates an instrument 410 into the top position, this rotation would guide the top instrument forward due to an advancing ridge 401 so one instrument would be active at a time. This design, as shown in FIG. 7A, also uses an inner gear 716 in order to provide individual rotation, as the top instrument 711 would articulate with this gear 716, which could be turned by the thumb to rotate the instrument.

Figure 5A:
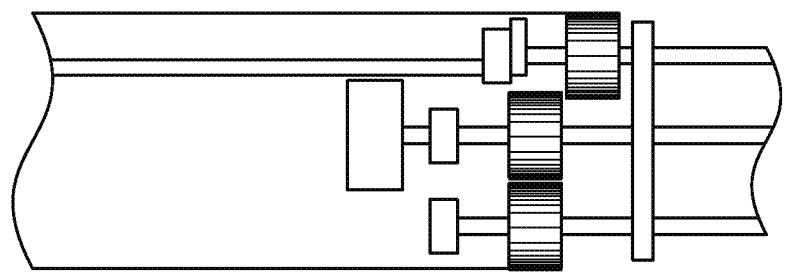
FIG. 5(A): An exemplary design for a spacer that keeps the instruments separate.
Figure 5B:
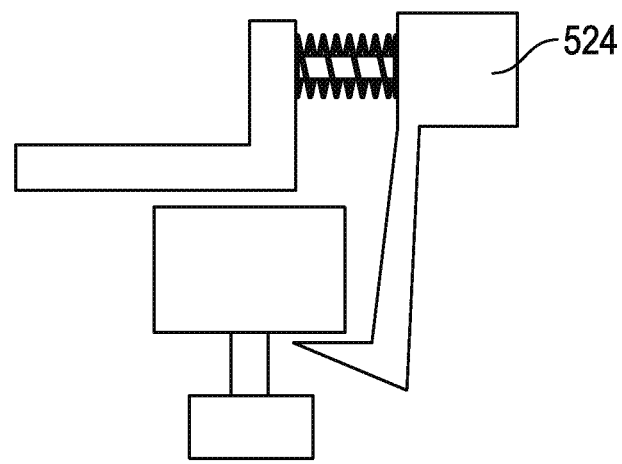
FIG. 5(B): An exemplary design of a button to release instruments from the sheath.
Figure 10A:
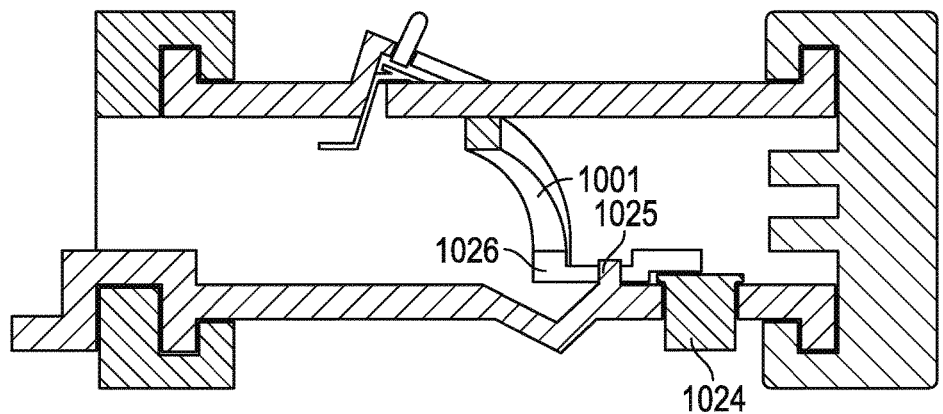
FIG. 10(A): An exemplary design of an instrument barrel cross section with release instrument button, turning knob, and electrocautery port. The button releases a spool from an advancing ridge.

In one embodiment, as shown in FIGS. 10A and 5B, the device may include a button 1024/524 which, when pushed, would allow an instrument to slide out, allowing you to put in another instrument. This would allow for single instrument exchange at a time. In one embodiment, the button would detach the turning disk, such that an instrument may be replaced mid-procedure.

In one embodiment, shown, for example, in FIG. 4, the proximal end of each instrument 410 would contain a spool 418 or ball (shown as 1103 in FIG. 11A) which would fit inside or on the advancing ridge 401 and push the instrument forward as it rotated up, and back as it rotated down; this piece may also interact with the handle 413 which would open and close each instrument when it was in the active position.

In another embodiment, we speculate that a magnetic ball at the end of each instrument on a ball hinge and a magnetic advancing ridge could work when paired with lower friction materials. We speculate that this would make the use of a spring unnecessary.

One embodiment may include a magnetic translational motion device, which adds to the translational motion component (TMC) of the barrel by utilizing a magnet to hold the instrument in place. This could include a regular ferromagnetic metal such as iron inset in the TMC with a turning disk that rotates the instrument into and out of active position. It could also include the use of an electromagnet set in the TMC, which would utilize current from the electrocautery connection port to rotate the instruments when a button is pushed. This will in turn replace the turning knob with a button and allow for the handle to be relocated from the bottom of the instrument to the back, which could be a more comfortable design.

One embodiment of a barrel 118 in which a sheath 108 would be placed is depicted in FIG. 1, where an advancing ridge 101 illustrates the motion instruments would take around the device. This embodiment illustrates an electrocautery capability connection 106 at top of the barrel 118, a locking mechanism 107 on the handle 113, and sheath 108 attachment at the front of the barrel 118.

Figure 2:
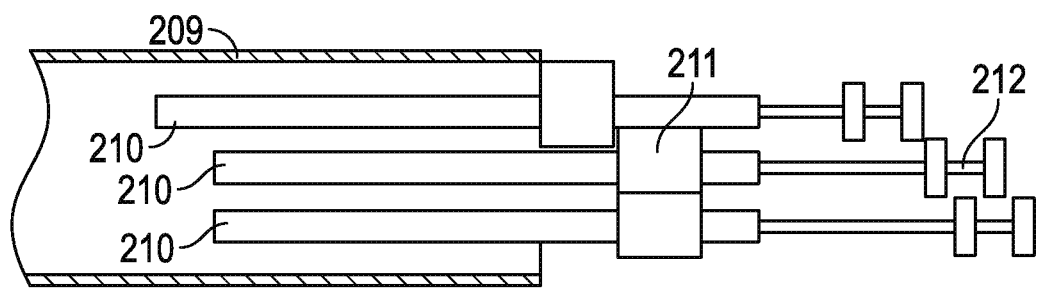
FIG. 2: An exemplary design of the proximal portion of the sheath with internal instruments.

One embodiment of a sheath 209 that would be placed in a barrel is depicted in FIG. 2. A sheath 209 surrounding three instruments 210 with child gears 211 and spool 212 at the proximal ends of instruments 210 as a connector. Movement of the spool 212 (controlled by opening and closing the handle) would be associated with opening and closing an instrument such as scissors.

Figure 3:
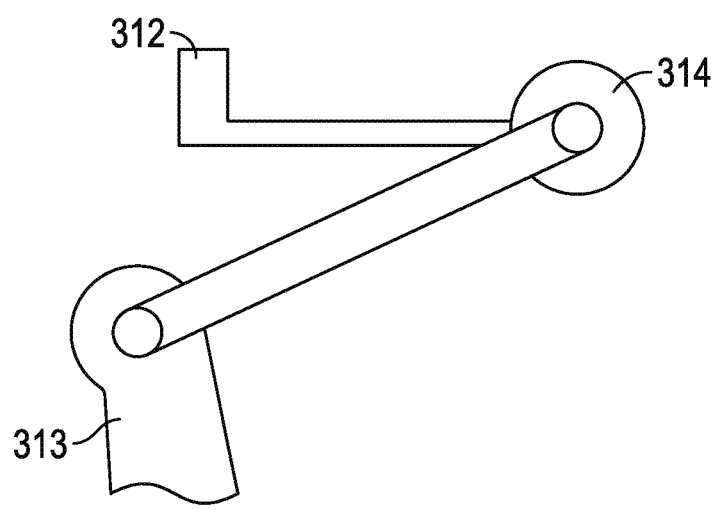
FIG. 3: An exemplary design of the mechanism that advances and retracts each instrument.

One embodiment of a piece that connects the handle of the device to the connector of an instrument is depicted in FIG. 3. As a handle 313 is moved, a hinge 314 translates movement to a spool via a connecting piece 312. This spool translates movement to a connector of an instrument thereby opening or closing an instrument.

Figure 12:
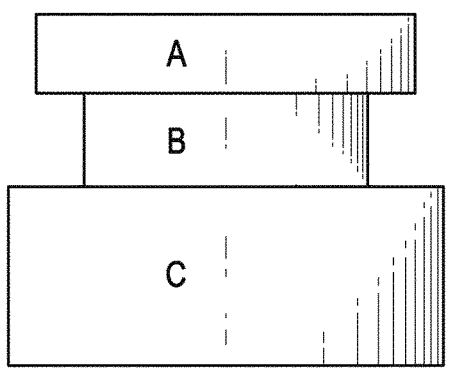
FIG. 12: An exemplary turning knob illustration.

One embodiment of a turning knob at the proximal end of the device (also shown as element 417 in FIG. 4) is depicted in FIG. 12. Surface A would be inside the device attached to the instruments in a sheath. Surface B corresponds to a female ridge that interfaces with a barrel. Surface C is on the outside of the barrel such that a user can rotate it.

Figure 9:
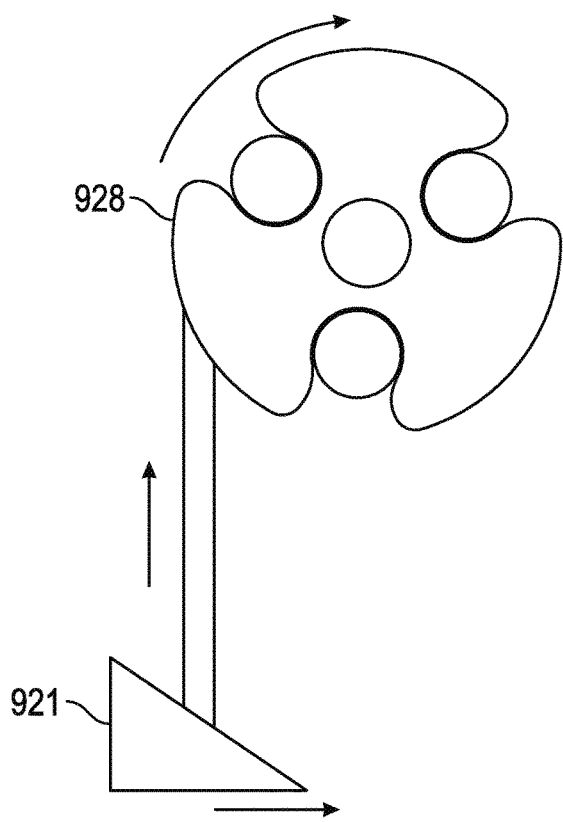
FIG. 9: An exemplary design of a mechanism to rotate the instruments in the device with a button.

In one embodiment, a button 921 as seen in FIG. 9 may be used to rotate a wheel 928 which turns instruments around in a sheath.

FIG. 4 depicts one embodiment with an advancing ridge 401 in the middle of the device. In this embodiment, a sheath 409 which holds the instruments is connected to a barrel 415. A gear 416 may be turned for instrument rotation by interfacing with child gears 411 attached to the instruments 410. A center rod 400 controlled via a turning knob 417 allows for instrument selection. A spool/ridge interface 418 guides the instruments 410 by the shape of the ridge 401. The ridge 401 curves along the wall of the barrel 415 toward the proximal end (6 o'clock position in the barrel 415) and then the distal end (12 o'clock position in the barrel 415). So as the gear 416 turns each instrument 410 via child gears 411, each instrument 410 advances or retracts based on the curve of the ridge. Those instruments that require opening and closing may be opened and closed by the spool/ridge interface 418 and a pushing rod 419 connected to a handle 413 via a hinge 420. Instruments 410 may be replaced by a cartridge release button 421. Finally, the barrel 415 has an electrocautery port 406 connected to the advanced instrument 410.

Figure 6:
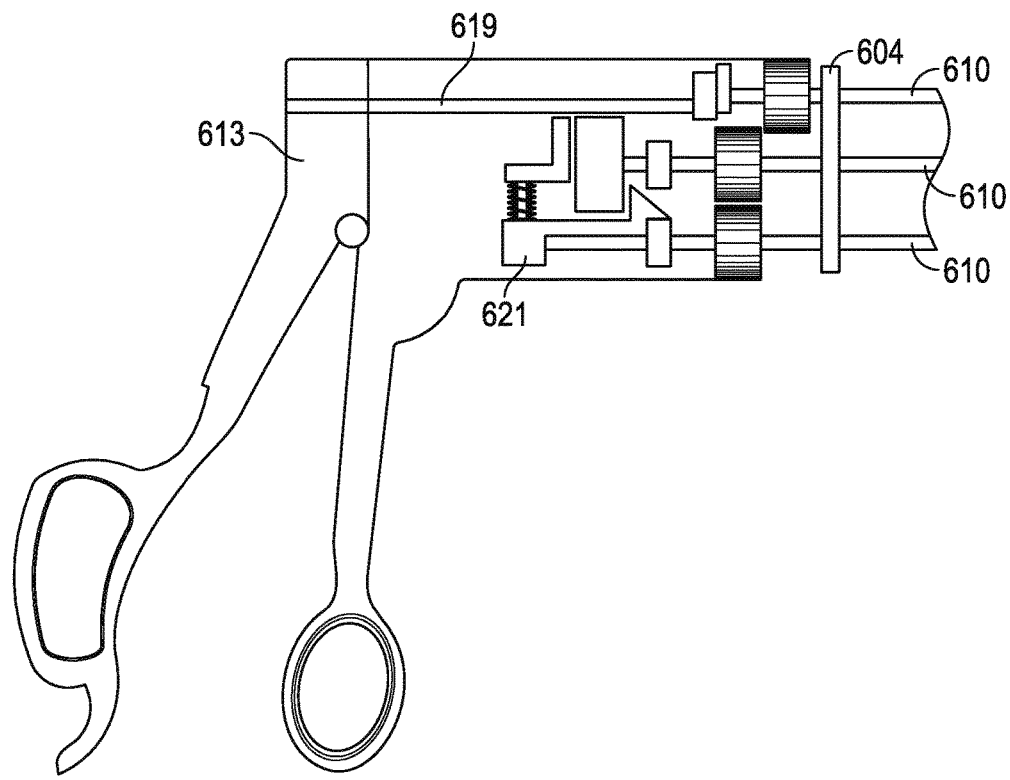
FIG. 6: An exemplary design of the proximal portion of the device containing a three-instrument cartridge with exposed spacer to change instruments, a rear handle, a linear rod to open/close instruments, and a button to release instruments.

FIG. 6 further depicts how instruments 610 are advanced and replaced in one embodiment. A turning disk 604 design is used with a turning rod (not pictured) to guide instrument selection. In one embodiment, a handle 613 may be located at the proximal end of the device with a button 621 to release an instrument cartridge which may hold multiple instruments in a single cartridge. A pushing rod 619 controlled by the handle 613 opens and closes instruments.

Figure 7B:
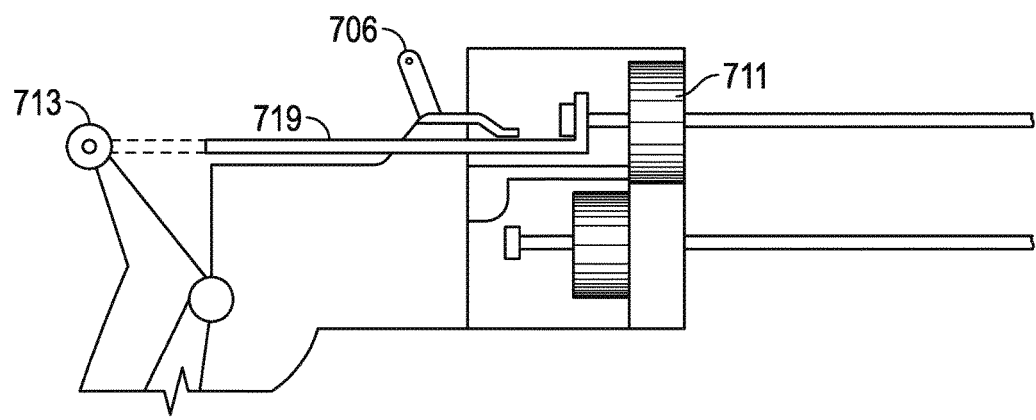
FIG. 7(B): An exemplary design of the proximal portion of the device with a pushing rod, handle and electrocautery port.
Figure 7C:
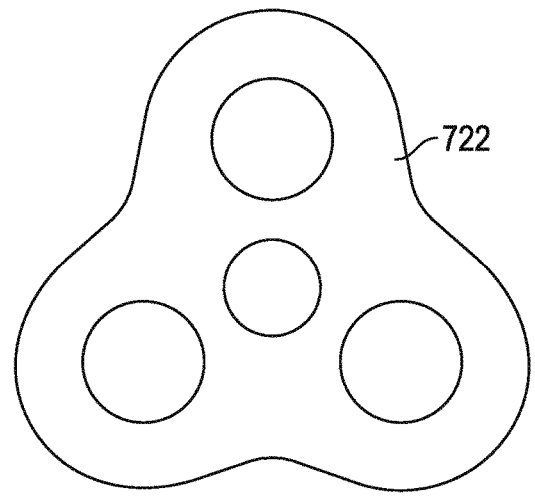
FIG. 7(C) An exemplary design of a spacer that keeps the instruments in position relative to each other.

FIG. 7A depicts a front view of a gear mechanism interface between parent gear 716 and child gears 711, where the advanced child gear is at position A and the retracted gears are at positions B and C allowing for single instrument being active at a time. FIG. 7B depicts an alternative electrocautery port position 706 and an alternative design of a pushing rod 719 with an alternative handle position 713. FIG. 7C depicts a spacer 722 to keep sufficient space between instruments.

Figure 8:
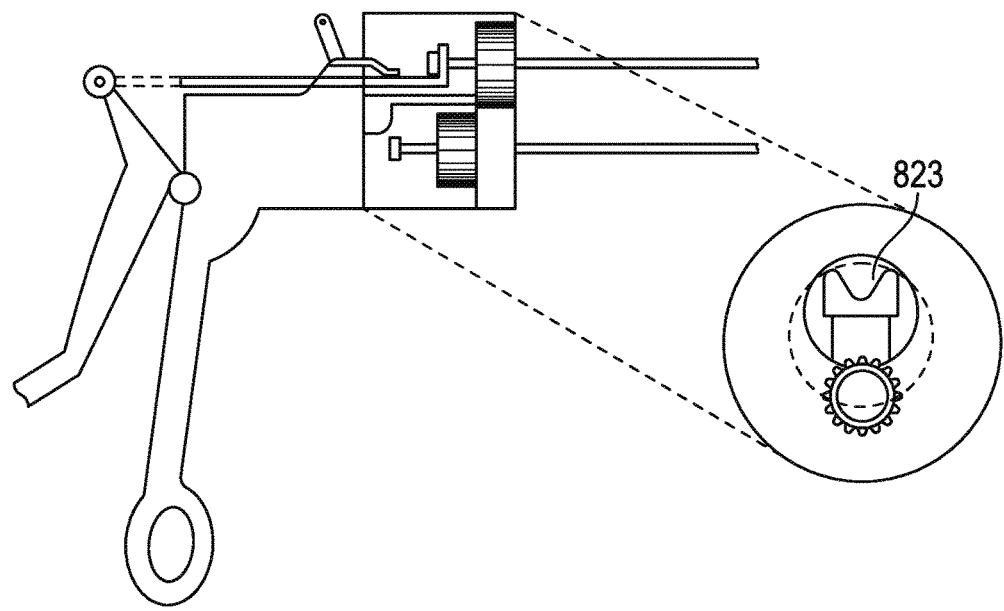
FIG. 8: An exemplary design for the proximal portion of the device with a focus on the saddle for connection of a pushing rod, and a means to allow for the opening and closing of individual instruments.

FIG. 8 depicts a saddle 823 for a connection of a pushing rod with instrument to allow for opening and closing of individual instruments.

Figure 10B:
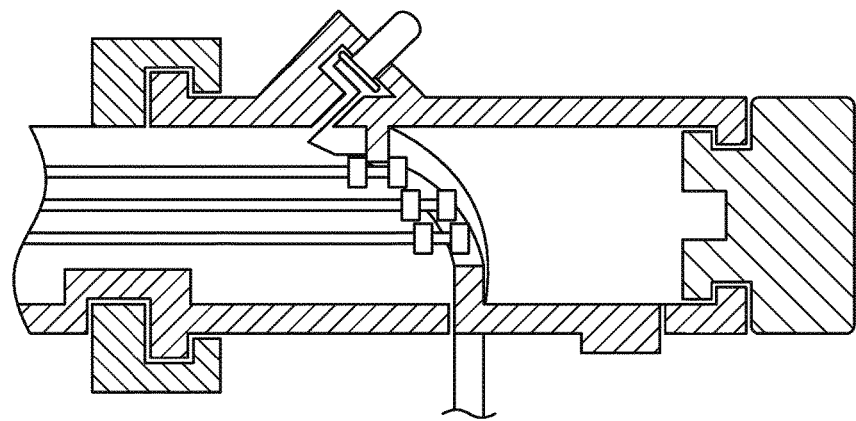
FIG. 10(B): An exemplary design of an instrument barrel cross section with the addition of instruments and spools.

FIGS. 10A and 10B depicts an advancing ridge 1001 in the middle of the device, which forces an individual instrument at the top to advance and the remaining instruments to retract. FIG. 10A specifically depicts a release button 1024 with spring loaded fulcrum 1025 is designed to lock/release individual instrument spool in place by completing/disconnecting section 1026 of advancing ridge 1001.

Figure 13:
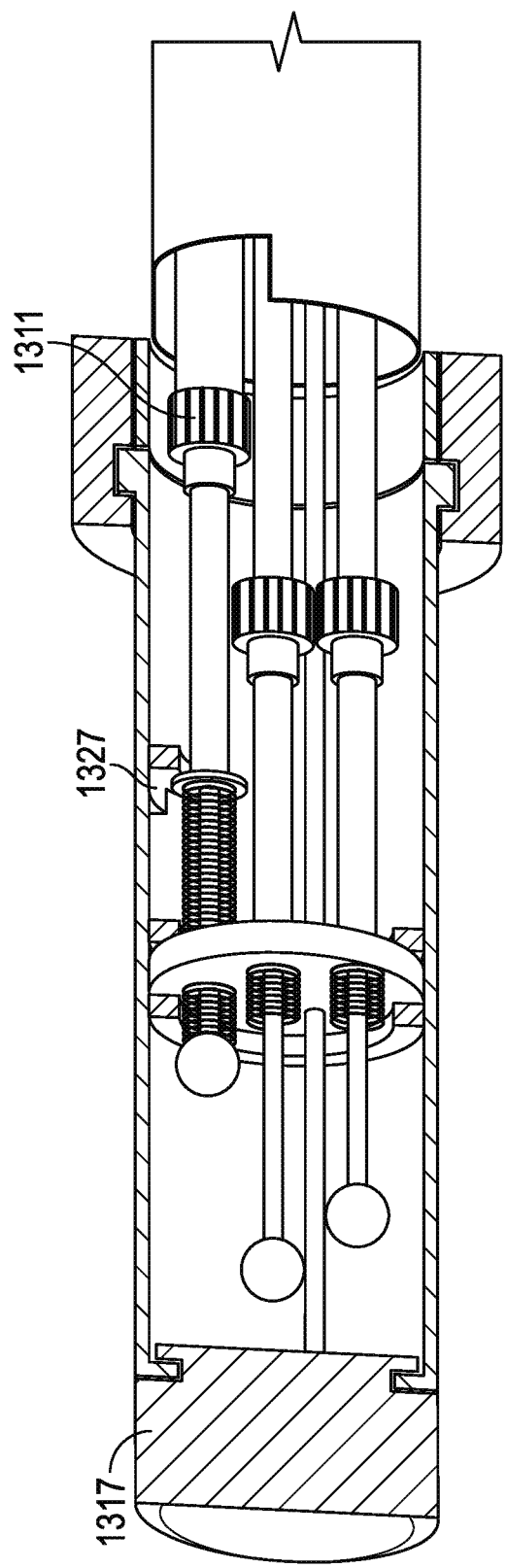
FIG. 13: An exemplary view of an interior of a barrel with a spring loaded cartridge.

FIG. 13 depicts a gear interface within the inhibitor fossa 1327. Here, an inner gear 1311 handles individual instrument rotation and a turning knob 1317 at the proximal end of the device allows for control of rotation.

Figure 14:
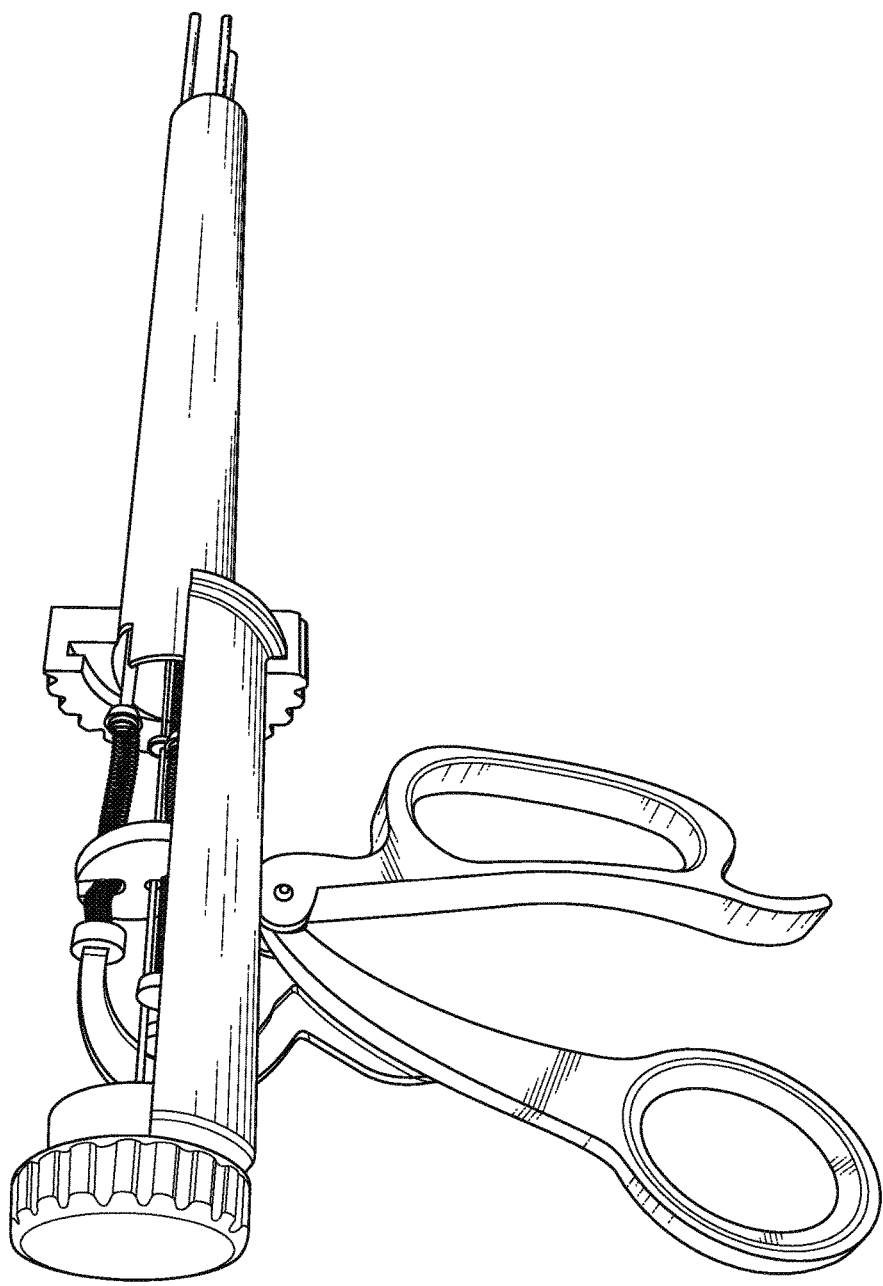
FIG. 14: An exemplary view of the cross section of the barrel showing the housing sheath geometry, and anchoring in relation to the instrument gears.

FIG. 14 shows an exemplary prototype of one design embodiment. Here instrument advancement/retraction is accomplished through use of springs and manual force application in conjunction with turning knob. Also shown is the use of instrument cartridges that fit into the device as a set of three instruments.

Figure 15:
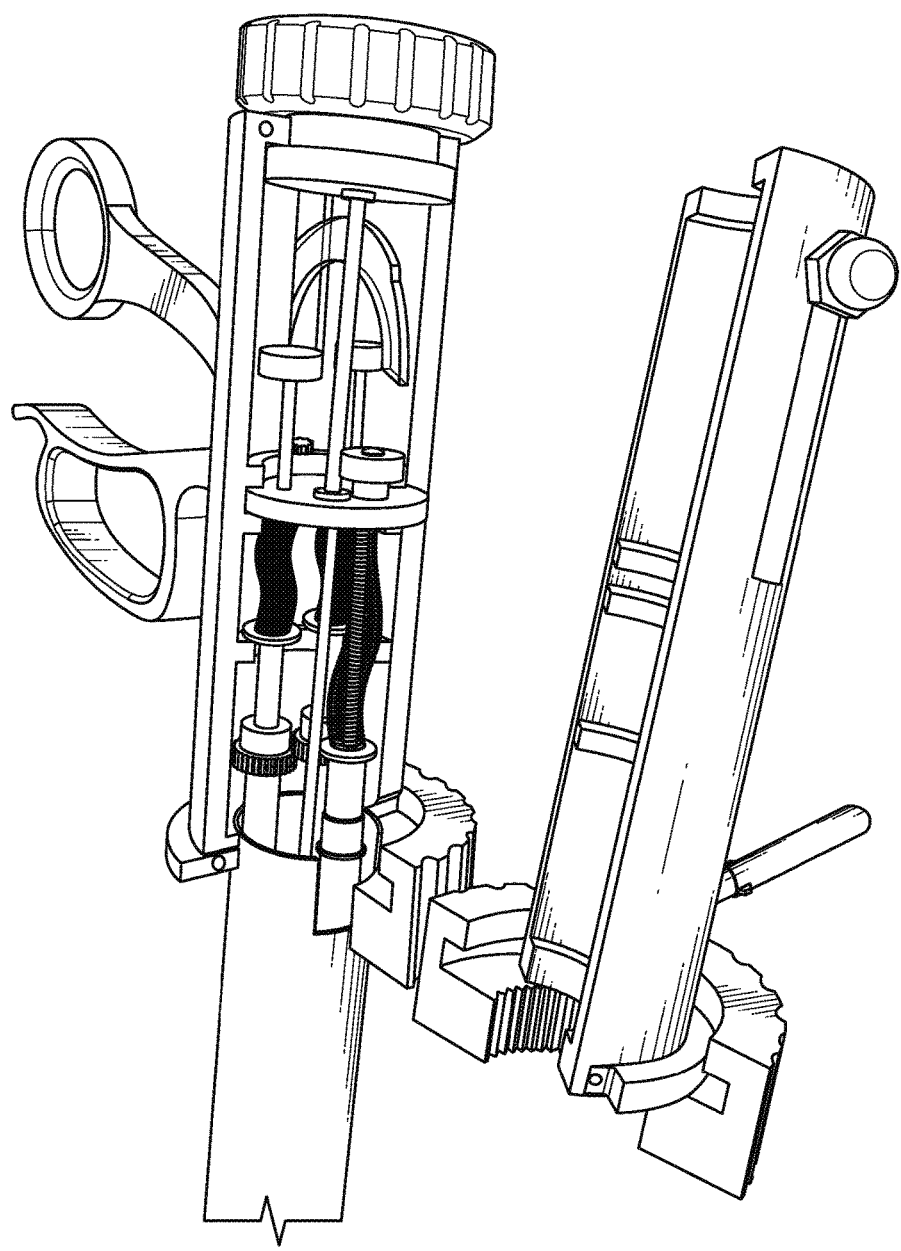
FIG. 15: An exemplary view of an unbalanced spring loaded cartridge inside a housing barrel.

FIG. 15 shows a different angle of the exemplary prototype shown in FIG. 14.

In one embodiment, springs provide forward motion. In another embodiment compressive foam provides forward motion.

In one embodiment, the outside parent gear, which rotates the individual advanced instrument at the top of the barrel, may be replaced with a dial. This dial may be concentric with the wall of the barrel of the instrument, and positioned on the side (either right or left) of the barrel. This will allow for a more compact design. By removing the outside parent gear, a large part of the bulk will be replaced by a slimmer rotation component. The dial must be large enough to interface with the child gear of the advanced instrument. In a preferred embodiment, the dial will be from 4 to 10 mm in diameter. The teeth of the dial will interface, and fit snuggly into, the teeth of the inner gear which is mounted on the outside of the sub-sheath of the individual instrument. This will allow the user to rotate the dial with a single finger, and the motion will then be transferred to the inner gear on the outside of the sub-sheath in the opposite direction, allowing for individual rotation.

In another embodiment, the turning disk will be partially exposed on the outside of the barrel. This will allow the user to rotate the turning disk at will, without the use of the turning knob. This method will reduce the bulk that makes up the turning disk and will further contribute to the compactness of the device by reducing the space in the back of the barrel. It will not only eliminate the need for the turning knob, but will also eliminate the space that was taken up by the portion of the turning rod stemming from the back of the turning disk and ending at the anchor point in the turning knob.

In some embodiments, the handle may be positioned at the bottom (as shown in FIG. 1). In some embodiments the handle may be positioned at the proximal end of the device (as shown in FIG. 6).

In another embodiment, a handgun style barrel may be employed where what is now a cylinder shaped instrument can be flattened with the exception of where the TMC is located on the barrel, this would result in a handgun like appearance, and would substantially reduce the size of the instrument.

Another embodiment may include a bipolar detection locking system so when instrument is closed around tissue, a circuit is completed which will lock the instrument to prevent the user from retracting the instrument while in use.

In one embodiment, each instrument has a basic retraction safety mechanism to assure that individual instruments cannot be accidentally retracted while still grasping tissue. This safety mechanism is intended to assure that no tissue/vessels/structures will be accidentally torn. This function is accomplished by: an inability of the instrument to initiate retraction if the graspers/instrument jaws are not completely closed (i.e., the instrument jaws cannot close because there is tissue between them).

In one embodiment bipolar tissue recognition is employed where the instrument recognizes a completed circuit when clamped down on tissue which disables the ability to retract. In one embodiment, a solenoid locking device requires that there is no resistance between the tips (e.g. poles, arms, jaws) of the instrument as a requisite for the instrument to be retractable. If there is no current across the tissue (meaning no tissue in the jaws of the device), then the solenoid "relaxes", allowing the "lock" to unhinge, so the individual device can retract. In another embodiment (the instrument which utilizes springs), it is physically impossible to retract the instrument when it is clamped down due to virtue of the design: in the absence of refraction, the "inhibitor fossa" or "inhibitor groove" (FIG. 13, 1327) prevents rotational motion of the advanced instrument. The advanced instrument simply cannot retract beyond the boundaries of the advancement plane while the jaws are open. FIG. 13 shows the inhibitor groove/fossa 1327 preventing retraction. In another embodiment within the device, the instrument center (or turning rod) is disabled from rotating within the barrel, which corresponds to the clamped position of the instrument. For example, when the pushing rod closes an individual instrument, an "instrument ridge" is engaged, preventing the turning rod from rotating, thereby preventing the engaged instrument from rotating into the retraction positions.

In another embodiment, instruments may be extended or shortened, which could also be automated. If a patient has a very large body mass index (BMI), or other physiologic characteristics, limitations, or variations, which make the instruments not quite long enough to effectively and safely manipulate the target tissues, the instruments can be extended for extra length as needed. This is also reversible, allowing the instruments to be shortened, so long as the engaged instrument does not retract into the sheath. In one embodiment, this is accomplished by using a differently sized sheath, and differently sized instruments.

Examples of Construction

The construction of the device may be broken down into different subcategories. The first category may be comprised of the same material, and have a similar construction method. Category one includes the turning knob, barrel (including any added buttons), handle, turning disk, parent gear, inner gears, and spacers and spools/spheres. Category two includes all items that are purchased from pre-manufactured parts and modified to specs such as the housing sheath, inner gears, individual instruments, pins, springs, and connections (electrocautery male adapter). Starting with the construction of category one, the components may be designed using 3 dimensional software, and then either milled, laser cut, casted, or printed into form using the range of materials described in this paper. If casting is used, it may be combined with a 3D printer, and printed with either ABS (Acrylonitrile butadiene styrene) or PLA (Polylactic Acid) thermoplastic.

The second category may have to be hand made with various tools. Starting with the housing sheath, a jig may be constructed to cut already manufactured thin walled tubing to a specified length, which may cover the entire length of the individual instruments. The jig can also be used to cut the tubing at a specified angle, whether custom is needed, or in increments of 15 degrees.

Moving on toward the individual instruments, initial instruments may be bought with a diameter range from 3 to 5 mm, and then modified by either removing its sub sheath and having all three sub sheaths replaced by the housing sheath, or by designing sub sheaths from premanufactured tubing that are thinner and more compact, allowing for more space efficiency. Next, the inner gears which interface with the parent gear may be either constructed using the method described in category one, or modified from existing gears to fit compactly within the barrel. Lastly the pins, ports and springs may be constructed and modified from raw materials.

The instruments main limiting dimension is the diameter of the outer sheath, which interfaces with the body during surgery; this diameter will be no larger than 10 mm in size, as is the current largest size surgeons use, and still contain all instruments within it. The length of the sheath will fall within the sizes commonly used in instrumentation today, between 200 mm for pediatric instruments and 400 mm in length for adult sizes. The dynamic dimensions of the handle should be between 1 cm ("closed handle") and 10 cm ("open handle"), but can be changed for more sensitive "tolerance" of the handle.

This device may be constructed with a variety of materials; the actual handle can be constructed of a low friction, high density and non-absorbent plastic such as but not limited to polyethylene (for disposable instruments) and polypropylene (for non-disposable autoclaveable instruments). Other plastics including but not limited to plastic, polyvinyl chloride and PTFE resin could be used. Other materials would also be included in construction of the handle including but not limited to electromagnets, ferromagnetic metals, as well as other metals commonly used in surgical settings like stainless steel and titanium, as well as alloys which allow for autoclaving/sterilization procedures. The sheath can be constructed of any biocompatible material including but not limited to cobalt chrome, titanium, or biocompatible polymer such as polyether ether ketone or pyrolytic carbon. Individual instruments will be constructed of metals including but not limited to stainless steel, titanium or high-density aluminum and will be coated in an insulating material such as but not limited to PTFE.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as a basis for the claims and as a representative basis for teaching one skilled in the art to employ the present invention in any appropriate manner.

A number of embodiments have been described. Nevertheless it will be understood that various modifications may be made without departing from the spirit and scope of the invention. Accordingly, other embodiments are included as part of the invention and may be encompassed by the attached claims. Furthermore, the foregoing description of various embodiments does not necessarily imply exclusion. For example, "some" embodiments, "exemplary" embodiments, or "other" embodiments may include all or part of "some," "other," and "further" embodiments within the scope of this invention.

What is claimed is:

1. A surgical device comprising:
  a barrel;
  a plurality of instruments wherein each of said plurality of instruments comprises a distal end and a proximal end and wherein said proximal ends of said plurality of instruments are located inside said barrel
  an advancing ridge located inside said barrel, wherein said proximal ends of said plurality of instruments are in connection with said advancing ridge, and wherein said advancing ridge is configured to move at least one of said plurality of instruments into an advanced position while allowing the other instruments of said plurality of instruments to remain in a retracted position; and
  a cartridge wherein said cartridge is comprised of said plurality of instruments and a turning disk, wherein said plurality of instruments pass through said turning disk, and wherein said cartridge is removably connected to said barrel and said turning disk is at least partially exposed to an exterior of said barrel.

2. The surgical device of claim 1 further comprising a cartridge release button wherein when engaged said cartridge release button is capable of disconnecting said cartridge from said barrel.

3. The surgical device of claim 1 further comprising a turning rod having a proximal end and a distal end, wherein said proximal end of said turning rod is located within said barrel, and wherein said turning rod is further connected to said turning disk.

4. The surgical device of claim 3 further comprising a turning knob wherein said turning knob is connected to said proximal end of said turning rod.

5. The surgical device of claim 1 further comprising:
  a plurality of spools wherein each of said plurality of spools is located on said proximal end of each of said plurality of instruments, and wherein each of said plurality of spools fit on said advancing ridge.

6. The surgical device of claim 5 further comprising a handle, wherein said handle comprises a first portion and a second portion; and wherein said first portion of said handle is located on an exterior of said barrel and said second portion of said handle is located on an interior of said barrel.

7. The surgical device of claim 6 wherein when said first portion of said handle is engaged, said second portion of said handle presses on said spool of said instrument in said advanced position and wherein said pressing translates movement to said distal end of said instrument.

8. The surgical device of claim 1 further comprising a plurality of spheres wherein each of said plurality of spheres is located on said proximal end of each of said plurality of instruments.

9. The surgical device of claim 8 further comprising a plurality of springs wherein each of said plurality of springs is located between each of said plurality of spheres and said turning disk.

10. The surgical device of claim 9 further comprising a handle, wherein said handle comprises a first portion and a second portion; and wherein said first portion of said handle is located on an exterior of said barrel and said second portion of said handle is located on an interior of said barrel.

11. The surgical device of claim 10 wherein, when said first portion of said handle is engaged, said second portion of said handle presses on said sphere of said instrument in said advanced position and wherein said pressing translates movement to said distal end of said instrument.

12. The surgical device of claim 10 further comprising a pushing rod wherein said second portion of said handle is connected to said pushing rod, and when said first portion of said handle is engaged, said second portion of said handle moves said pushing rod resulting in said pushing rod pressing on said sphere of said instrument in said advanced position and wherein said pressing translates movement to the said distal end of said instrument.

13. The surgical device of claim 1 further comprising an electrocautery port.

14. A surgical device comprising:
a barrel;
a plurality of instruments wherein each of said plurality of instruments comprises a distal end and a proximal end and wherein said proximal ends of said plurality of instruments are located inside said barrel;
an advancing ridge located inside said barrel, wherein said proximal ends of said plurality of instruments are in connection with said advancing ridge, and wherein said advancing ridge is configured to move at least one of said plurality of instruments into an advanced position while allowing the other instruments of said plurality of instruments to remain in a retracted position;
a cartridge wherein said cartridge is comprised of said plurality of instruments and a turning disk wherein said plurality of instruments pass through said turning disk, and wherein said cartridge is removably connected to said barrel;
a plurality of spools wherein each of said plurality of spools is located on said proximal end of each of said plurality of instruments, and wherein each of said plurality of spools fit on said advancing ridge;
a handle, wherein said handle comprises a first portion and a second portion and wherein said first portion of said handle is located on an exterior of said barrel and said second portion of said handle is located on an interior of said barrel; and
a pushing rod wherein said second portion of said handle is connected to said pushing rod, and when said first portion of said handle is engaged, said second portion of said handle moves said pushing rod resulting in said pushing rod pressing on said spool of said instrument in said advanced position and wherein said pressing translates movement to the said distal end of said instrument.

15. A surgical device comprising:
a barrel:
a plurality of instruments wherein each of said plurality of instruments comprises a distal end and a proximal end and wherein said proximal ends of said plurality of instruments are located inside said barrel;
an advancing ridge located inside said barrel, wherein said proximal ends of said plurality of instruments are in connection with said advancing ridge, and wherein said advancing ridge is configured to move at least one of said plurality of instruments into an advanced position while allowing the other instruments of said plurality of instruments to remain in a retracted position; and
a plurality of spheres wherein each of said plurality of spheres is located on said proximal end of each of said plurality of instruments, wherein said plurality of spheres are connected to said advancing ridge via a magnetic force.

16. A surgical device comprising:
a barrel;
a plurality of instruments wherein each of said plurality of instruments comprises a distal end and a proximal end and wherein said proximal ends of said plurality of instruments are located inside said barrel;
an advancing ridge located inside said barrel, wherein said proximal ends of said plurality of instruments are in connection with said advancing ridge, and wherein said advancing ridge is configured to move at least one of said plurality of instruments into an advanced position while allowing the other instruments of said plurality of instruments to remain in a retracted position; and
a parent gear wherein said parent gear is located at a distal end of said barrel and is turnable about said barrel.

17. The surgical device of claim 16 wherein each of said plurality of instruments further comprise a child gear and wherein when one of said plurality of instruments is in said advanced position, said child gear and said parent gear are in contact.

18. A surgical device comprising:
a plurality of instruments wherein each of said plurality of instruments comprises a distal end and a proximal end;
a means for surrounding said proximal ends of said plurality of instruments;
a means for advancing each of said plurality of instruments wherein said advancing means is located inside said surrounding means, wherein said proximal ends of said plurality of instruments are in connection with said advancing means, and wherein said advancing means is configured to move at least one of said plurality of instruments into an advanced position while allowing the other instruments of said plurality of instruments to remain in a retracted position;
a plurality of means for linking said distal ends of each of said plurality of instruments to said advancing means wherein each of said linking means is located on said distal end of each of said plurality of instruments, and wherein each of said plurality of linking means are in contact with said advancing means, and wherein said plurality of linking means and said advancing means are connected via a magnetic force.

19. A surgical device comprising:
a plurality of instruments wherein each of said plurality of instruments comprises a distal end and a proximal end;
a means for surrounding said proximal ends of said plurality of instruments;
a means for advancing each of said plurality of instruments wherein said advancing means is located inside said surrounding means, wherein said proximal ends of said plurality of instruments are in connection with said advancing means, and wherein said advancing means is configured to move at least one of said plurality of instruments into an advanced position while allowing the other instruments of said plurality of instruments to remain in a retracted position;

a plurality of means for linking said distal ends of each of said plurality of instruments to said advancing means wherein each of said linking means is located on said distal end of each of said plurality of instruments, and wherein each of said plurality of linking means are in contact with said advancing means;

a means for containing said plurality of instruments in a predetermined configuration wherein said containing means is comprised of said plurality of instruments and a means for maintaining a constant spacing among each of the plurality of instruments wherein said plurality of instruments pass through said spacing means and wherein said containing means is removably connected to said surrounding means; and a plurality of means for forcing said linking means to remain in contact with said advancing means, wherein each of said forcing means is located between said plurality of linking means and said spacing means.

* * * * *